United States Patent [19]

Lafon

[11] 4,271,194
[45] Jun. 2, 1981

[54] SEDATIVE COMPOSITIONS CONTAINING (3,4-DICHLOROPHENYLSULPHINYL)-ACETAMIDOXIME AND ITS ADDITION SALTS AND METHOD OF USE

[75] Inventor: Victor Lafon, Paris, France

[73] Assignee: Laboratoire L. Lafon, Maisons-Alfort, France

[21] Appl. No.: 48,179

[22] Filed: Jun. 13, 1979

Related U.S. Application Data

[63] Continuation of Ser. No. 899,860, Apr. 25, 1978, abandoned.

[30] Foreign Application Priority Data

Apr. 29, 1977 [FR] France .................................. 77 13043

[51] Int. Cl.³ .................. A61K 31/155; C07C 123/00
[52] U.S. Cl. ...................................... 424/326; 564/229
[58] Field of Search ......... 260/564 G, 501.14, 501.12, 260/343.7; 424/280, 316, 319, 326; 564/229

[56] References Cited

U.S. PATENT DOCUMENTS

| | | | |
|---|---|---|---|
| 3,334,137 | 8/1967 | Bruderlein et al. | 260/564 G |
| 3,736,356 | 5/1973 | Trenner | 260/564 G |
| 4,013,776 | 3/1977 | Lafon | 260/564 G |

*Primary Examiner*—Natalie Trousof
*Assistant Examiner*—L. Hendriksen

[57] ABSTRACT

The compound (3,4-Dichlorophenylsulphinyl)-acetamidoxime, of the structural formula:

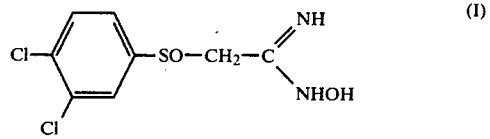

and its addition salts with acids.

These compounds are useful in therapy as substances acting on the central nervous system.

2 Claims, No Drawings

SEDATIVE COMPOSITIONS CONTAINING (3,4-DICHLOROPHENYLSULPHINYL)-ACETAMIDOXIME AND ITS ADDITION SALTS AND METHOD OF USE

This is a continuation, of application Ser. No. 899,860, filed Apr. 25, 1978 now abandoned.

The present invention provides, by way of new industrial products, (3,4-dichlorophenylsulphinyl)-acetamidoxime and its addition salts with acids. These products are useful in therapy as substances which act on the central nervous system.

The invention accordingly includes a method of treating a patient suffering from a disorder of the central nervous system, comprising administering to said patient a therapeutically effective dose of a product according to this invention.

(3,4-Dichlorophenylsulphinyl)-acetamidoxime has the formula

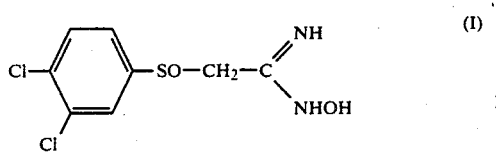

and can be prepared by a process analogous to that described in Belgian Pat. No. 833927, in particular by oxidising (3,4-dichlorophenylthio)-acetamidoxime using $H_2O_2$. The addition salts with acids can be obtained by reacting the free base with an inorganic or organic acid. Amongst the acids which can be used this purpose, there may be mentioned, in particular, hydrochloric, sulphuric, nitric, phosphoric, formic, acetic, fumaric, maleic, lactic, tartaric, malic, ascorbic, salicyclic, aspartic glutamic, benzoic and oxalic acids.

The invention also provides a therapeutic composition comprising, together with a physiologically acceptable excipient, at least one compound chosen from (3,4-dichlorophenylsulphinyl)-acetamidoxime and its non-toxic addition salts with acids.

There now follows a synthesis example and a summary of pharmacodynamic and clinical experiments using the product thereof.

EXAMPLE

Preparation of (3,4-dichlorophenylsulphinyl)-acetamidoxime hydrochloride

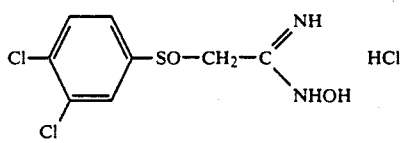

Code No.: CRL 40,412

(a) (3,4-Dichlorophenylthio)-acetonitrile 17.9 g (0.10 mol) of 3,4-dichlorobenzenethiol are mixed in the cold with a solution of 4.1 g of sodium hydroxide (about 0.1 mol) in 50 ml of water. The mixture is heated to 60°–70° C. and 7.5 ml (0.12 mol; 20% excess relative to the 3,4-dichlorobenzenethiol) of chloroacetonitrile are added dropwise. The whole is then heated under reflux for about 30 minutes and cooled, the oil which has formed is extracted with ether, the ether solution is washed with dilute sodium hydroxide solution and water, until the pH of the wash waters is neutral, and dried over $SO_4Mg$, the $SO_4Mg$ is filtered off, the ether is evaporated off and the expected nitrile, which is in the form of a chromatographically pure oil, is collected.

Weight = 30.2 g.
Yield = 100%.

(b) (3,4-Dichlorophenylthio)-acetamidoxime hydrochloride

The nitrile derivative obtained as indicated above is taken up with 100 ml of n-butanol, an aqueous solution (50 ml) of 0.25 mol of hydroxylamine base (obtained by neutralising 17.5 g of hydroxylamine hydrochloride with 25 g of $CO_3HK$ in water) is added, the whole is heated at the reflux temperature of the butanol/water mixture for about 3 hours, the butanol/water mixture for about 3 hours, the butanol/water mixture is evaporated off and the residue is taken up with water. The amidoxime base precipitates and is drained and dried. 24.9 g (yield = 99%) of (3,4-dichlorophenylthio)-acetamidoxime (instantaneous melting point = 88° C.) are thus collected. The corresponding hydrochloride is prepared in ethyl acetate by adding a solution of hydrochloric acid in ethanol to a solution of the base. After drying, 25.8 g (0.09 mol) of (3,4-dichlorophenylthio)-acetamidoxime hydrochloride are collected.

Yield = 90%.
Instantaneous melting point = 148°–150° C.

(c) CRL 40,412

25.8 g (0.09 mol) of (3,4-dichlorophenylthio)-acetamidoxime hydrochloride are mixed with 100 ml of acetic acid and 8 ml of $H_2O_2$ of 110 volumes strength (at 20° C.). It is observed that the mixture gradually becomes warm and that the sulphide simultaneously dissolves. The reaction mixture is then kept at 40°–45° C. and the course of the reaction is followed by chromatography. The acetic acid is evaporated off when all the sulphide has been oxidised. The residue is taken up with acetone and CRL 40,412 crystallises. It is recrystallised from a mixture of acetone and isopropanol (1:1 v/v), drained and dried. 18.9 g of CRL 40,412 are thus collected.

Yield = 66%.
Instantaneous melting point = 175°–180° C. (with decomposition).

In the experiments described below, the compound CRL 40,412 was administered to the animals intraperitoneally, in aqueous solution, in a volume of 20 ml/kg in the case of mica and 5 ml/kg in the case of rats, unless otherwise stated.

A. TOXICITY

In the case of mice, CRL 40,412 causes the appearance of convulsions, followed by death in 5 minutes, at doses of 1,024 and 512 mg/kg; at a dose of 256 mg/kg, hyper-reactivity followed by sedation is observed, and the appearance of a few convulsions and respiratory depression is also observed, death occurring 2 hours after administration of CRL 40,412; the $LD_0$ (maximum non-lethal dose) is of the order of 230 mg/kg; at a dose of 128 mg/kg, sedation and respiratory depression are observed; at doses of 64 and 32 mg/kg, only the sedative effect is observed (sedation lasting for 3 hours).

In the case of rats, at doses of 8 mg/kg to 32 mg/kg, it is found that the fear reaction increases for 30 minutes and that this is followed by a sedative effect.

B. EFFECT ON THE CENTRAL NERVOUS SYSTEM

(1) Interaction with amphetamine

Batches of 6 rats receive an intraperitoneal injection of amphetamine (2 mg/kg) 30 minutes after administration of CRL 40,412. At the two strongest doses, CRL 40,412 causes a potentiation reflected in the duration of the amphetamine stereotypes.

In order to test whether this potentiation was real or whether it was only due to interference with the amphetamine, the effect of CRL 40,412 on the amphetamine stereotypes was investigated in the case of rats (6 per dose) which had been pre-treated with Proadifen (Code No.: SKF 525A; systematic nomenclature: β-diethylaminoethyl 2,2-diphenylpentanoate). In the case of the pre-treated rats, it is found that CRL 40,412 no longer potentiates the amphetamine stereotypes.

(2) Effect on the motility

Spontaneous motility 30 minutes after administration of CRL 40,412, the mice (6 per dose, 12 comparison animals) are placed in an actimeter, where their motility is recorded for 30 minutes. It is found that, at doses of 16 and 64 mg/kg, CRL 40,412 causes a significant decrease in the spontaneous motility.

Under the same operating conditions, CRL 40,412, administered to mice gastrically (in aqueous solution in a volume of 20 ml/kg), leaves the motor activity virtually unchanged at doses of 16 mg/kg, 32 mg/kg and 64 mg/kg; at a dose of 128 mg/kg, it causes hypomotility.

Motility reduced by habituation to the cage

After remaining for 18 hours in the actimeters, the mice receive CRL 40,412. Immediately afterwards, they are replaced in their cages and, 30 minutes later, the recording of the motility starts and is continued for 30 minutes (6 mice per dose, 11 comparison animals). It is observed that CRL 40,412 does not cause any resumption of locomotion in the case of mice which are habituated to their cages. It should be noted that the batch of comparison animals exhibited an abnormally high residual motility.

Motility reduced by hypoxia treatment

CRL 40,412 is administered to groups of mice 30 minutes before subjecting them to anoxia by pressure reduction (depression of 600 mm Hg in 90 seconds, return to normal pressure in 45 seconds). Following this manipulation, the animals are placed in an actimeter, where their motility is recorded for 10 minutes. It is observed that, at doses of 16 mg/kg, 32 mg/kg and 64 mg/kg, CRL 40,412 causes a distinct improvement in the motor recovery of mice which have been subjected to anoxia by pressure reduction. At a dose of 128 mg/kg, this effect appears less clearly.

(3) Effect on asphyxiating anoxia

Batches of mice receive CRL 40,412 30 minutes before being injected intraperitoneally with gallamine triiodoethylate (Flaxedil) at a dose of 32 or 48 mg/kg, and the time required for the appearance of convulsive attacks and the occurrence of death is noted.

(α) Testing the activity by intraperitoneal administration (a) Flaxedil 32 mg/kg At doses of 32 and 64 mg/kg, CRL 40,412, administered intraperitoneally, moderately retards the appearance of the convulsions, but clearly increases the time required for mortality to occur.

(b) Flaxedil 48 mg/kg

CRL 40,412 did not retard the appearance of the convulsions at any of the doses used, but at doses of 32, and especially 64 mg/kg, it enables mice, the respiration of which has been blocked by a curarising agent, to survive for a longer time.

(β) Investigation of the activity after gastric administration

At doses of 64 and 128 mg/kg, CRL 40,412, administered gastrically, retards the occurrence of mortality due to Flaxedil which has been administered at a dose of 32 mg/kg.

(4) Conclusion

All the results of the experiments which have been given above, show that CRL 40,412 improves the performance of animals, the behaviour of which has been changed by various hypoxia treatments (anoxia by pressure reduction, and asphyxia by a curarising agent such as Flaxedil). Furthermore, the sedative effect and the motor recovery persist after gastric administration of CRL 40,412.

C. CLINICAL EXPERIMENTS

The clinical experiments made it possible to test the results of the pharmacodynamic experiments, namely that CRL 40,412 is a sedative agent and that its indication in therapy is for the treatment of diseases of the central nervous system and, more particularly, for the treatment of aggressiveness.

CRL 40,412 gave good clinical results as an antiaggression agent when it was administered in the form of tablets or capsules each containing 20 mg of active ingredient, at a rate of 3 tablets or capsules per day.

We claim:

1. A therapeutic sedative composition useful in the treatment of aggressiveness which contains, together with a physiologically acceptable excipient, at least one compound chosen from (3,4-dichlorophenyl-sulphinyl)-acetamidoxime and its pharmaceutically acceptable acid addition salts.

2. A method of treating a patient for aggressiveness, comprising administering to said patient a therapeutically effective dose of (3,4-dichlorophenylsulphinyl)-acetamidoxime or a non-toxic acid addition salt thereof.

* * * * *